United States Patent [19]

Carter et al.

[11] Patent Number: 5,447,237
[45] Date of Patent: Sep. 5, 1995

[54] MEDICAL TOTE AND TRAY

[76] Inventors: Richard L. Carter, P.O. Box 25, Nedrow, N.Y. 13120; Nancy J. Redmond, 300 Merritt Ave., Syracuse, N.Y. 13207

[21] Appl. No.: 307,170

[22] Filed: Sep. 16, 1994

[51] Int. Cl.[6] .............................................. A61B 19/02
[52] U.S. Cl. ................................. 206/570; 206/370; 206/806
[58] Field of Search ................ 220/751; 206/570, 571, 206/363, 370, 438, 557, 806

[56] References Cited

U.S. PATENT DOCUMENTS

| | | | |
|---|---|---|---|
| 4,053,280 | 10/1977 | Salisbury | 206/363 |
| 4,085,845 | 4/1978 | Perfect | 206/363 X |
| 4,796,790 | 1/1989 | Hamilton | 206/570 X |
| 5,108,000 | 4/1992 | Stoll et al. | 206/806 X |
| 5,143,243 | 9/1992 | Colling | 206/370 X |
| 5,145,063 | 9/1992 | Lee | 206/370 X |

Primary Examiner—Jacob K. Ackun
Attorney, Agent, or Firm—George R. McGuire

[57] ABSTRACT

A caddy or tote for containing and transporting medical equipment and supplies in a hospital environment. The tote comprises an open-topped container having a centrally disposed handle for carrying, and hook and brace members for supporting the container on the head, foot or siderails of a hospital bed. A tray is detachably connected to the container in either of a stored position, below the container bottom wall, or a deployed position, extending outwardly from the upper edge of the front wall of the container, to support medical instruments or other items. Contact area between the tote and bed or other surfaces within the room is minimized to reduce the possibility of nosocomial infection. A secondary container may be clipped to the primary container and is adapted to receive used medical sharps in a styrofoam block impregnated with liquid viricidal bactericide.

19 Claims, 3 Drawing Sheets

MEDICAL TOTE AND TRAY

BACKGROUND OF THE INVENTION

The following patent application is based upon and/or contains material included in Disclosure Document No. 319392 dated Oct. 26, 1992, which is requested to be retained.

The present invention relates to articles for carrying and supporting items of medical equipment, and more specifically to a container with detachable tray for bedside use.

Transmission of nosocomial infection (nosocomial infection is infection acquired within a health care facility) within hospitals and other health-care facilities has always been and remains a major health threat. In 1991 there were some 2 million traceable cases of hospital-transmitted disease, resulting in some 16,000 deaths, in the U.S. alone. Additionally, it addresses the critical issue of increasing antibiotic resistant organisms such as methicillin-resistant S. aureus (MRSA), vancomycin resistant enterococci (VRE) and incurable viruses like HIV. In 1992 alone, an estimated 13,300 hospital patients died of antibiotic resistant infections. In many cases, bacteria from which the illness emanates are transferred from personnel or medical equipment and supplies, including articles used to contain and/or transport such equipment and supplies, to bed linens or other items in the immediate vicinity of those who are thus exposed. Constant cleaning and disinfecting of possibly contaminated items and the areas with which they may or do come in contact is inconvenient and expensive, if not impossible to effectively implement.

Thus, hospital safety may be enhanced by reducing to a minimum surface contact between items where nosocomial infection may occur. Also, facilitating accessibility to and control of needles, catheters, dressings, etc. to medical personnel reduces the possibility of mishandling or other errors which may degrade overall safety standards. Accordingly, availability of proper means for carrying, deploying and storing items used in bedside medical procedures is a prime requirement in any program of healthcare safety both in reducing nosocomial infection and preventing accidents.

It is a principal object of the present invention to provide a novel and improved medical tote for equipment and supplies which both enhances worker efficiency, safety and reduces the possibility of nosocomial infection.

A further object is to provide an article which serves both as a container for holding and carrying medical items and as a bed-attachable means for deploying such items for ready access while performing various medical procedures.

It is a further object of the present invention to provide an increased proactive approach to the 1992 OSHA Regulations relating to Occupational Exposure to Bloodborne Pathogens (Final Rule 29 CFR Part 1910.1030).

Another object is to provide a medical tote and tray which may be attached to a bed with minimal area of mutual surface contact.

A still further object is to provide a medical tote incorporating a readily accessible container for used needles which contributes to safety of handling, use and disposal thereof.

Other objects will in part be obvious and will in part appear hereinafter.

SUMMARY OF THE INVENTION

In accordance with the foregoing objects, the invention contemplates a medical tote including an open-topped receptacle having a bottom wall, four side walls and a centrally located handle. Affixed to or formed integrally with one of the side walls are two arms with hooked upper ends, suitable for engagement with a bed rail to temporarily support the tote at either side or either the head or foot of the bed. Brace means are provided for selectively extending between the tote and another portion of the bed, such as a second rail, parallel to and either above or below the first rail.

A planar, rectangular tray has a pair of legs extending perpendicularly therefrom along one side. The tray may be secured when not in use adjacent the outer surface of the bottom wall of the tote. The tray legs are inserted in pockets adjacent the side wall on the opposite side of the tote from the hooked arms so that the tray extends horizontally outwardly from the side of the tote farthest from the bed.

A needle container includes an external clip for selective attachment to one of the tote sidewalls. The container encloses styrofoam, or other suitable material, impregnated with a viricidal bactericide into which used needles may be inserted. A short tab or wedge extends from an upper edge of the container over the styrofoam to ensure the latter is retained within the container until intentionally removed for disposal and replacement.

BRIEF DESCRIPTION OF THE DRAWINGS

The foregoing and other features of the invention will be more readily understood and fully appreciated from the following Detailed Description, taken in conjunction with the accompanying drawings, wherein.

DETAILED DESCRIPTION

Figure 1:
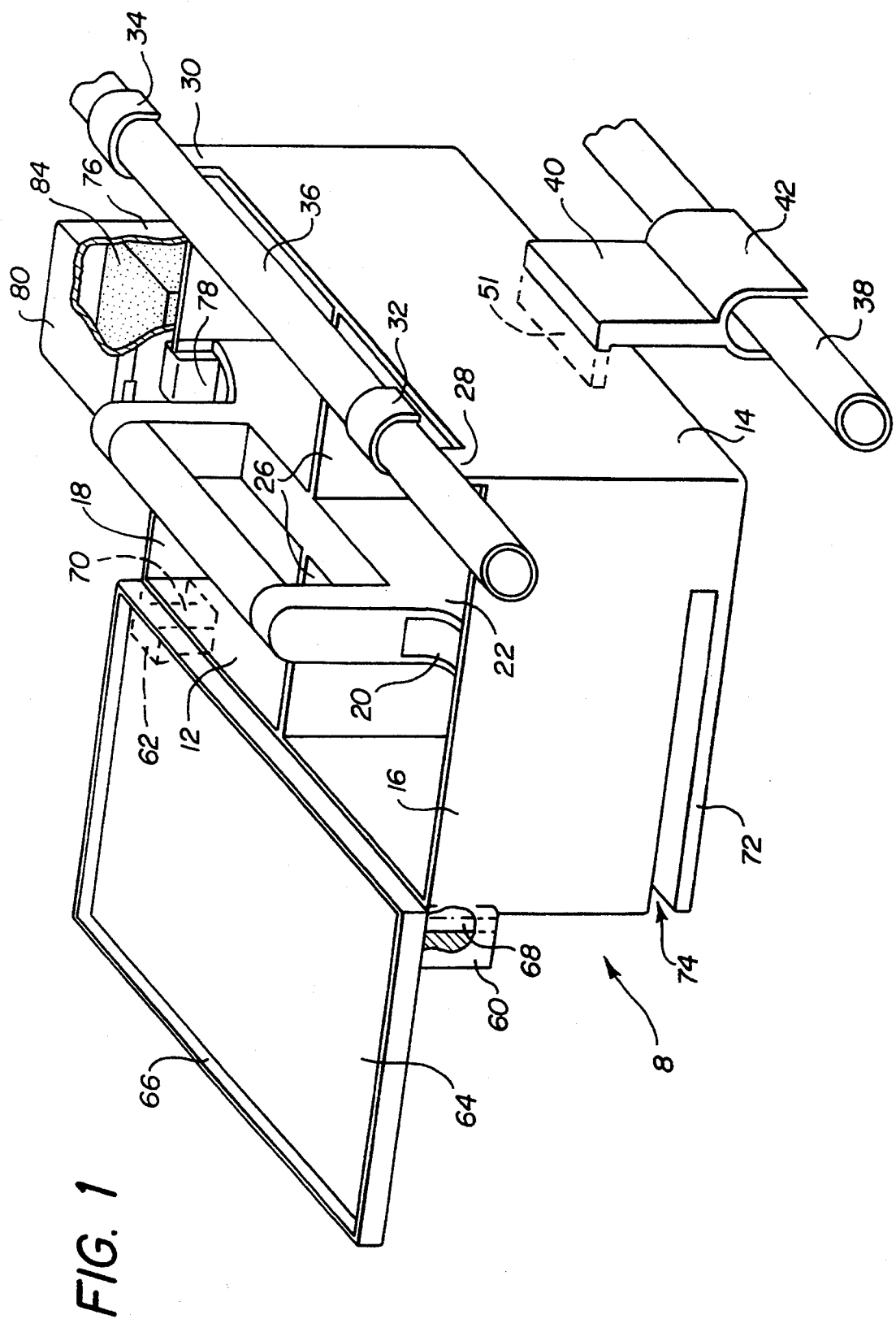
FIG. 1 is an upper perspective view of the medical tote, including a detachable tray, the tote being shown in a first position of attachment to a bed rail, and the tray shown in a deployed position.

Referring now to the drawings, the medical tote or caddy comprises an open-topped container 8 having bottom wall 10, front and rear walls 12 and 14, respectively, and end walls 16 and 18. The front, rear and end walls have coplanar upper edges. A pair of parallel, internal walls 20 and 22 extend between end walls 16 and 18. Internal walls 20 and 22 are of decreased height in the portions adjacent end walls 16 and 18, providing small compartments therebetween, handy for carrying rolls of tape. Handle 24 extends upwardly from internal walls 20 and 22, centrally of the four side walls. Other internal walls, such as those indicated by reference numeral 26, may be provided to compartmentalize container 8 as desired, consistent with the type and configuration of medical equipment and supplies to be stored and carried therein.

Figure 2:
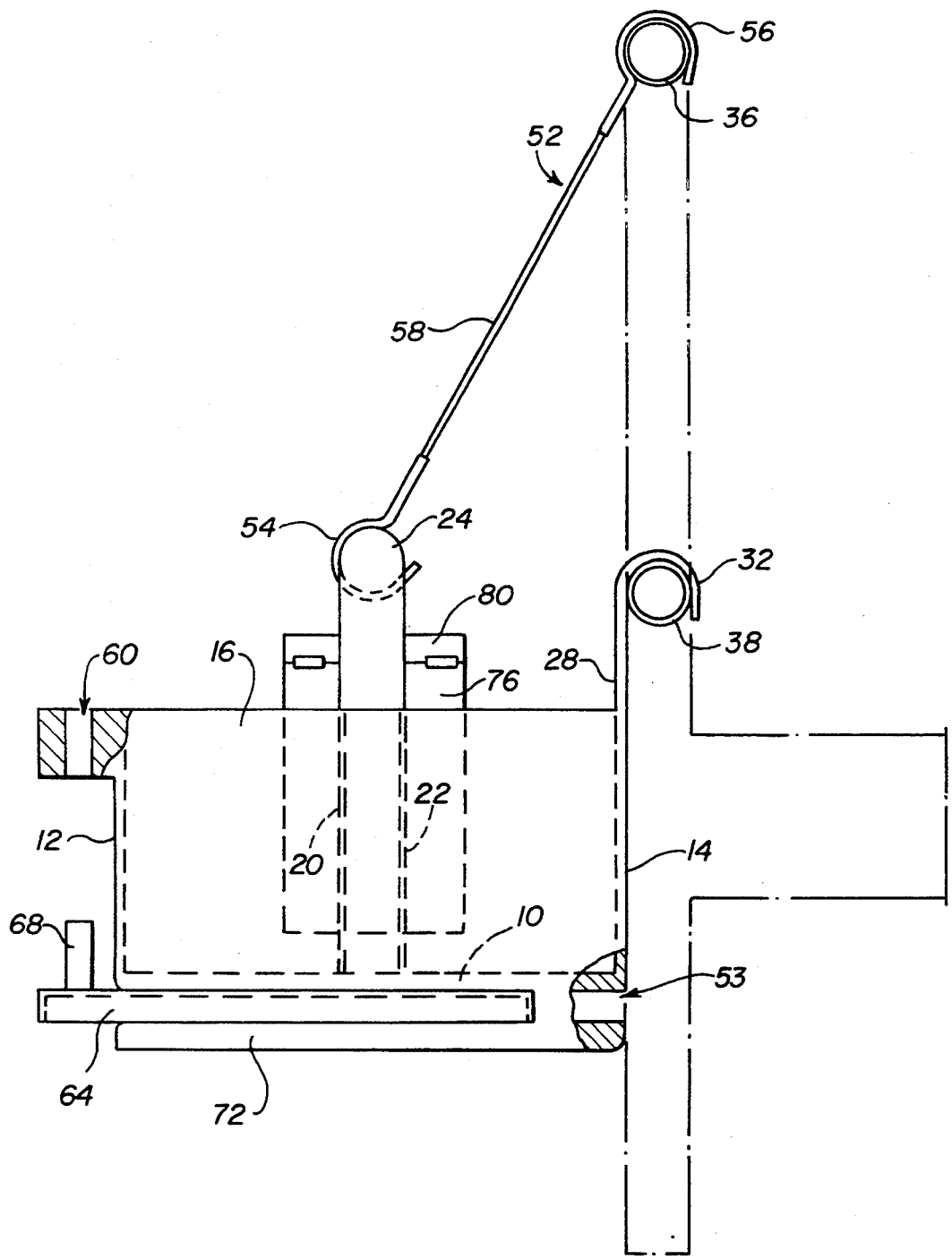
FIG. 2 is an end elevational view of the tote and tray with the latter in a stored position, and the tote attached to the bed rail in a second position.

A pair of arms 28 and 30, having hooked ends 32 and 34, respectively, extend upwardly from rear wall 14 adjacent opposite sides thereof. Arms 28 and 30 are formed integrally with or fixedly attached to rear wall 14. As shown in FIGS. 1 and 2, hooked ends 32 and 34 are adapted for engagement over one of the horizontal members 36, 38 forming portions of a conventional hospital bed siderail, or the head or foot of the bed, thereby supporting container 8 at any one side of the bed.

In FIG. 1, hooked ends 32 and 34 are engaged over upper rail member 36, and rigid strut 40 extends between a position at the center of the juncture of bottom and rear walls 10 and 16 and lower rail member 38. Curved end 42 of strut 50 rests upon rail member 38 to hold container 8, in conjunction with arms 28 and 30, in a firmly supported position at bedside. Since most hospital bed siderails are of standard dimensions, strut 40 may be of fixed length or, if desired, the strut may be of telescoping or other known configuration, such as the support strut of the bedside tray of U.S. Pat. No. 4,357,881, to provide adjustability of length. Strut 40 may be, for example, hingedly connected to container 8, or may be detachably secured thereto only during use by means such as the illustrated tab 51 on the strut being frictionally inserted into open slot 53 at the lower, rear edge of container 8.

In FIG. 2, hooked ends 32 and 34 are engaged over lower rail member 38 and support member 52 extends between handle 24 and upper rail member 36. Member 52 has hooks 54 and 56 at opposite ends, joined by flexible portion 58 which may, if desired, be of an elastic material to provide some tolerance in length. Hooks 54 and 56 are releasably engaged over handle 24 and upper rail member 36, respectively, and support member 52 is removed when not in use.

A pair of open-topped pockets 60 and 62 are formed by suitable wall means integral with front wall 12 and/or side walls 16 and 18. Substantially planar, rectangular tray 64, preferably having peripheral lip 66 on one surface, may be selectively placed in either of a deployed position (FIG. 1) or a stored position (FIG. 2 with respect to container 8. Legs 68 and 70 are formed integrally with or fixedly attached to the surface opposite that having lip 66 adjacent each end of one of the long edges. Tray 64 is placed in the deployed position by inserting legs 68 and 70 into the openings in pockets 60 and 62 so that tray 64 extends outwardly from the upper edge of front wall 12 of container 8. In this position, tray 64 is conveniently located to support medical instruments, equipment or supplies for use by nursing and ancillary medical personnel.

Figure 3:
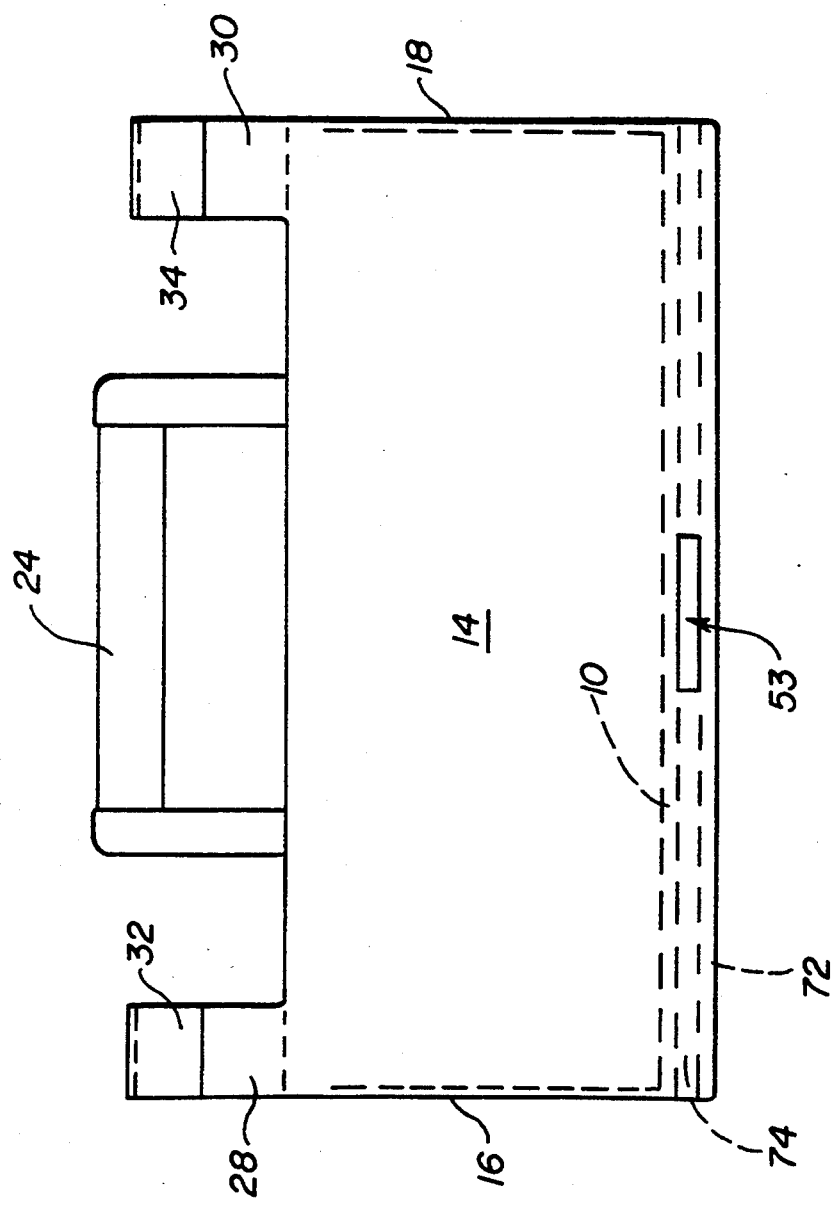
FIG. 3 is a rear elevational view of the tote.

Shelf-like portion 72 extends forwardly from the lower, rear area of container 8 in parallel, spaced relation to the outer surface of bottom wall 10. Tray 64 is placed in the stored position, as shown in FIG. 2, by sliding movement into space 74 (FIGS. 1 & 3) between bottom wall 10 and portion 72, with legs 68 and 70 extending upwardly, adjacent front wall 12. If desired, other means such as one or more spring clips or cooperable Velcro strips on tray 64 and container 8, may be provided for retaining tray 64 in an appropriate stored position.

One of the items which may be advantageously carried by the tote is a smaller or secondary container 76 which may be detachably secured to one of the walls of container 8 by sliding spring clip 78 of secondary container 76 over one of the upper wall edges. Secondary container 76 has a bottom and four side walls, and preferably a hingedly attached cover 80. The intended purpose of secondary container 76 is to provide a safe and readily accessible means for receiving used hypodermic needles or other sharps.

Figure 4:
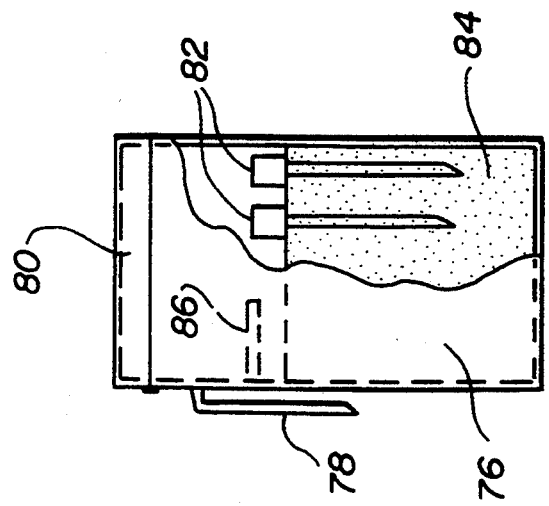
FIG. 4 is a side elevational view, with portions broken away, of a container for detachable connection to the tote.

As seen in the broken-away portion of FIG. 4, styrofoam (or other suitable material) 84 is positioned within and substantially fills the cross-sectional area of container 76. Styrofoam 84 is impregnated with an appropriate viricidal bactericide to minimize the possibility of nosocomial infection from used needles inserted therein. Tab (or wedge) 86 extends from an upper wall edge of container 76 over the top of styrofoam 84 to prevent inadvertent dislodgement or removal of styrofoam 84 from container 76.

From the foregoing it may be seen that the present invention not only provides an extremely convenient and efficient means for containing, transporting and utilizing medical materials of many types, but also contributes greatly to hospital safety. It will be noted that the tote may be supported by a bedrail with the tray deployed to accept instruments, supplies, etc. with minimal surface contact between the tote and any items in the hospital room. This contrasts with common past practices of placing items directly upon bed linens, tables above or at the side of the bed, or other locations in the room which could lead to nosocomial infection between the bedside area and items brought in and out of such area. Use of the secondary container eliminates the necessity for medical personnel to walk from bedside to a remote sharps container while carrying contaminated sharps (needles, razors, etc.).

What is claimed is:

1. A medical tote for containing and transporting medical instruments, supplies, and the like to and from hospital bedsides, said tote comprising:
    a) wall means defining a primary container wherein said instruments, supplies, and the like, may be placed for selective retrieval;
    b) handle means for lifting and carrying said primary container;
    c) a substantially planar tray;
    d) first means for detachably securing said primary container in a predetermined orientation to a hospital bed;
    e) second means for detachably securing said tray to said primary container, with the latter in said predetermined orientation, in a deployed position extending outwardly from said primary container in a substantially horizontal plane; and
    f) third means for detachably securing said tray to said primary container in a stored position closely adjacent to one of said primary container wall means.

2. The invention according to claim 1 wherein said first means comprises at least one hook member for engagement over a first, horizontal bedside rail.

3. The invention according to claim 2 wherein said first means further comprises brace means for detachable connection between said primary container and a second bedside rail, parallel to and at a different vertical height than said first rail.

4. The invention according to claim 3 wherein said brace means extends between said primary container wall means and said second bedside rail.

5. The invention according to claim 3 wherein said brace means extends between said handle means and said second bedside rail.

6. The invention according to claim 1 wherein said primary container wall means comprise a bottom, front, rear and two end walls and said one wall means is said bottom wall.

7. The invention according to claim 6 wherein said third means comprises retaining means on at least one of said tray and said primary container for releasably maintaining said tray in said stored position, adjacent and substantially parallel to the outer surface of said bottom wall.

8. The invention according to claim 7 wherein said retaining means comprises at least one retainer member fixed with respect to and extending in adjacent, spaced relation to at least a portion of said bottom wall outer surface for sliding movement of said tray between said retainer member and said bottom wall outer surface in movement of said tray to and from said stored position.

9. The invention according to claim 6 wherein said first means comprises at least one hook member affixed to said rear wall for engagement over a horizontal bedside rail.

10. The invention according to claim 9 wherein each of said front, rear and end walls have an upper edge and said second means comprises cooperable engagement means on said tray and said primary container for positioning said tray to extend outwardly from said front wall in said deployed position.

11. The invention according to claim 10 wherein said tray extends outwardly substantially from said upper edge of said front wall in said deployed position.

12. The invention according to claim 11 wherein said engagement means comprise a pair of legs fixedly attached to said tray and means on said primary container for slideably accepting said legs to position said tray in said deployed position.

13. The invention according to claim 10 wherein said third means comprises cooperable fastening means for releasably maintaining said tray in said stored position, adjacent and substantially parallel to said bottom wall.

14. The invention according to claim 10 wherein said upper edges are in a common plane and said handle means is positioned above said common plane substantially centrally of the periphery of said upper edges.

15. The invention according to claim 1 and further including secondary container means, significantly smaller than said primary container, having secondary wall means defining a cavity adapted to receive medical needles.

16. The invention according to claim 15 and further including a styrofoam block positioned within said cavity for receiving said needles.

17. The invention according to claim 16 wherein said styrofoam block is impregnated with a viricidal bactericide.

18. The invention according to claim 15 and further including means for detachably securing said secondary container means to said primary container.

19. The invention according to claim 18 wherein said securing means comprises a spring clip affixed to said secondary container means.

* * * * *